(12) United States Patent
Burkholz et al.

(10) Patent No.: US 10,758,720 B2
(45) Date of Patent: Sep. 1, 2020

(54) CLOSED IV ACCESS DEVICE WITH Y-PORT NEEDLE-FREE CONNECTOR

(71) Applicant: CareFusion 303, Inc., San Diego, CA (US)

(72) Inventors: Jonathan Karl Burkholz, Salt Lake City, UT (US); George Michel Mansour, Pomona, CA (US); Jonathan Yeh, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 268 days.

(21) Appl. No.: 15/289,049

(22) Filed: Oct. 7, 2016

(65) Prior Publication Data

US 2017/0120028 A1    May 4, 2017

Related U.S. Application Data

(60) Provisional application No. 62/247,690, filed on Oct. 28, 2015.

(51) Int. Cl.
*A61M 39/10* (2006.01)
*A61M 39/26* (2006.01)
(Continued)

(52) U.S. Cl.
CPC .......... *A61M 39/10* (2013.01); *A61M 39/105* (2013.01); *A61M 39/22* (2013.01);
(Continued)

(58) Field of Classification Search
CPC ........ A61M 39/105; A61M 2039/1066; A61M 2039/1072; A61M 2039/1077;
(Continued)

(56) References Cited

U.S. PATENT DOCUMENTS

| | | |
|---|---|---|
| 4,655,752 A | 4/1987 | Honkanen et al. |
| 5,125,903 A | 6/1992 | McLaughlin et al. |

(Continued)

FOREIGN PATENT DOCUMENTS

| | | |
|---|---|---|
| CN | 101534882 A | 9/2009 |
| CN | 206587229 U | 10/2017 |

(Continued)

OTHER PUBLICATIONS

International Search Report and Written Opinion for Application No. PCT/US2016/056056, dated Jan. 24, 2017, 15 pages.

(Continued)

*Primary Examiner* — Nathan R Price
*Assistant Examiner* — Melissa A Snyder
(74) *Attorney, Agent, or Firm* — Morgan, Lewis & Bockius LLP

(57) ABSTRACT

A multi-port connector such as a closed intravenous (IV) access device with a y-port needle-free connector may be provided. The multi-port connector may include a main housing with a longitudinal axis, a needle free connector disposed along the longitudinal axis, and a y-port extending from a sidewall of the main housing at an angle that is non-parallel with the longitudinal axis. The needle-free connector may include a compressible sealing member that, when compressed opens a first fluid pathway from a first port, through a chamber within the housing, and to an output port. The y-port may be fluidly coupled to the chamber and the output port.

27 Claims, 21 Drawing Sheets

(51) Int. Cl.
  *A61M 39/24* (2006.01)
  *A61M 39/22* (2006.01)
  *A61M 39/16* (2006.01)
(52) U.S. Cl.
  CPC ............ *A61M 39/24* (2013.01); *A61M 39/26* (2013.01); *A61M 39/16* (2013.01); *A61M 2039/1038* (2013.01); *A61M 2039/1072* (2013.01); *A61M 2039/1083* (2013.01); *A61M 2039/1088* (2013.01)
(58) Field of Classification Search
  CPC .. A61M 2039/1083; A61M 2039/1088; A61M 39/10
  See application file for complete search history.

(56) References Cited

U.S. PATENT DOCUMENTS

| | | | | |
|---|---|---|---|---|
| 5,676,346 | A | * | 10/1997 | Leinsing ............... A61M 39/26 251/149.1 |
| 6,213,978 | B1 | * | 4/2001 | Voyten ............... A61M 25/0606 604/164.01 |
| 7,815,168 | B2 | | 10/2010 | Vangsness et al. |
| 2002/0193752 | A1 | | 12/2002 | Lynn |
| 2003/0209681 | A1 | * | 11/2003 | Leinsing ............ A61M 39/045 251/149.1 |
| 2006/0027270 | A1 | * | 2/2006 | Truitt .................... A61M 39/02 137/843 |
| 2006/0089604 | A1 | | 4/2006 | Guerrero |
| 2008/0086097 | A1 | * | 4/2008 | Rasmussen ......... A61M 39/045 604/266 |
| 2013/0237925 | A1 | | 9/2013 | Trainer et al. |
| 2014/0276463 | A1 | | 9/2014 | Mansour et al. |

FOREIGN PATENT DOCUMENTS

| | | |
|---|---|---|
| EP | 2042214 A1 | 4/2009 |
| EP | 2623153 A1 | 8/2013 |
| WO | WO-2008043069 A2 | 4/2008 |
| WO | WO-2014009823 A1 | 1/2014 |
| WO | WO-2015100135 A2 | 7/2015 |

OTHER PUBLICATIONS

European Office Action for Application No. 16785631.9, dated Mar. 6, 2019, 4 pages.
Chinese Office Action for Application No. 201610957798.8, dated Apr. 20, 2020, 14 pages.
Extended European Search Report for Application No. 20154664.5, dated Apr. 8, 2020, 8 pages.

* cited by examiner

CLOSED IV ACCESS DEVICE WITH Y-PORT NEEDLE-FREE CONNECTOR

CROSS-REFERENCE TO RELATED APPLICATIONS

The present application claims the benefit of priority under 35 U.S.C. § 119 as a nonprovisional of U.S. Provisional Patent Application Ser. No. 62/247,690 entitled "Closed IV Access Device With Y-Port Needle-Free Connector," filed on Oct. 28, 2015, the disclosure of which is hereby incorporated by reference in its entirety for all purposes.

TECHNICAL FIELD

The present disclosure generally relates to needle-free connectors, and more particularly to needle-free connectors with multiple ports.

BACKGROUND

Needle-free ports are commonly used in intravenous (IV) fluid delivery systems. In some situations, it is desirable to be able to provide multiple different fluids to a patent. Needle-free ports with multiple input ports have been developed. However, if care is not taken when connecting to and disconnecting from such conventional multiple input devices, risk of microbial ingress, colonization, and blood reflux upon disconnection can be high. It would therefore be desirable to be able to provide improved multi-port connectors.

SUMMARY

Multi-port connectors can sometimes be provided with a secondary fluid path that enters distally to the valve components of a primary fluid path. However, in this configuration, a complex internal fluid geometry can be created that prevents adequate flushing, and can therefore present a risk of microbial colonization within the multi-port connector. In accordance with various aspects of the present disclosure, a multi-port connector may be provided that includes a primary fluid path and a secondary fluid path such as a y-port that accesses the connector in such a way that improves flushability of the connector and therefore reduces the risk of microbial colonization.

In accordance with some aspects, a needle-free connector is provided that includes a housing; a first input port in the housing; a second input port in the housing; a chamber within the housing that is fluidly coupled to the first input port and the second input port; and an output port that is fluidly coupled to the chamber.

In accordance with other aspects, a housing for a needle-free connector is provided, the housing including a central elongate portion having a longitudinal axis; a needle-free valve formed along the longitudinal axis; an output port formed along the longitudinal axis; an open Luer port comprising an extension from a sidewall of the central elongate portion; and a chamber within the central elongate portion, wherein the chamber is fluidly coupled to the needle-free valve, the open Luer port, and the output port.

In accordance with other aspects, a patient fluid delivery system is provided that includes at least one fluid source, configured to contain a fluid; tubing configured to provide the fluid to a patient; and a needle-free connector configured to couple between the at least one fluid source and the tubing, the needle-free connector including a housing; a first input port in the housing; a second input port in the housing; a chamber within the housing that is fluidly coupled to the first input port and the second input port; an output port that is fluidly coupled to the chamber; and a compressible sealing member within the housing, the compressible sealing member having an uncompressed state in which the compressible sealing member seals the first input port and a compressed state that allows a continuous fluid pathway between the first input port and the output port.

In accordance with other aspects, a method is provided that includes providing a first fluid from a first input port of a needle-free connector through a chamber of the connector to an output port of the connector; and providing a second fluid from a second input port of the connector through the chamber to the output port.

In accordance with other aspects, a needle-free connector is provided that includes a lower housing having a sidewall; a needle-free valve having an upper housing, and a compressible sealing member disposed between the upper housing and the lower housing; a y-port formed from a portion of the lower housing that extends at a non-parallel angle from the sidewall of the lower housing; and an output port in the lower housing, the output port fluidly coupled to the needle-free valve and the y-port.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims, Various aspects of the subject technology will now be disclosed according to particular but non-limiting examples. Various embodiments described in the present disclosure may be carried out in different ways and variations, and in accordance with a desired application or implementation.

Systems and methods are provided for the infusion of a medical fluid, (e.g., a saline solution or a liquid medication) to patients using an intravenous (IV) catheter that is connected, though an arrangement of flexible tubing and fittings (commonly referred to as an "IV set") to a source of fluid (e.g., an IV bag or a syringe). The fittings may include interconnectable male and female needleless connectors having a "Luer taper" conforming to an International Standards Organization (ISO) standard or other needleless connectors. Connectors may have a self-sealing feature to prevent leakage of fluid from the attached tubing when the connector is decoupled from a mating connector.

Figure 1:
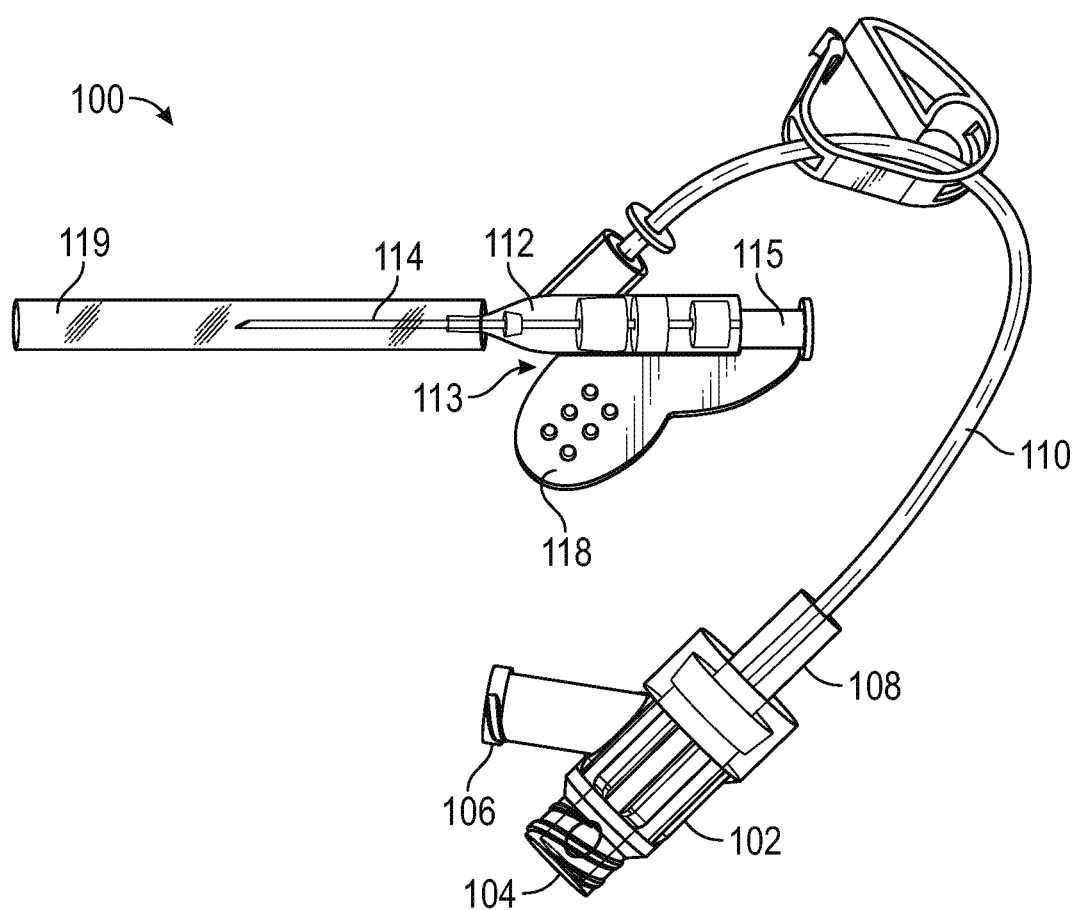
FIG. 1 illustrates an example of an IV system having a needle-free connector, in accordance with aspects of the present disclosure.

FIG. 1 illustrates an example of a patient fluid delivery system 100. As shown, system 100 may be implemented as a closed system vascular access device such as a closed intravenous catheter system having patient interface such as a catheter assembly 113 and having a needle-free connector 102 with a first input port 104, a second input port 106, and an output port 108. In the example of FIG. 1, the needle-free connector (NFC) 102 is attached via tubing 110 to catheter assembly 113. Catheter assembly 113 may include a needle hub 115 and a catheter adapter 112. Catheter assembly 113 may include a catheter 114 with an associated introducer needle that passes through the catheter adapter from the needle hub. The catheter 114 and associated introducer needle are shown in FIG. 1 within a protective sheath 119 (e.g., a removable cover for the needle).

Catheter adapter 112 may be integrally or removably connected to the tubing 110. Needle hub 115 may be removably coupled to catheter adapter 112, Needle hub 115 may include a grip portion (implemented as a paddle grip 118 in FIG. 1). Needle hub 115 may be configured to attach to the proximal side of the needle, both of which may be removed after insertion and placement of the catheter.

Needle huh 115 may be provided with a paddle grip 118 or may be provided with other types of grips such as a straight grip or a ported grip and/or an extension set as would be understood by one skilled in the art. The catheter assembly of FIG. 1 is merely illustrative. In other embodiments, a needle-free connector 102 may be coupled (e.g., via tubing 110) to other types of catheter systems. Some examples of catheter systems that may be fluidly coupled to needle-free connector 102 (e.g., via tubing) are described in U.S. Pat. Nos. 5,935,110, 6,638,252, and 8,337,461, all of which are hereby incorporated by reference herein in their entireties.

Needle-free connector 102 may be provided as an integrated component of the peripheral IV catheter system or may be provided separately and connected to tubing 110 of peripheral IV catheter system. Needle-free connector 102 may include first input port 104 implemented with a needle-free valve and second input port 106 implemented as a Luer access y-port. As described in further detail hereinafter, input port 104 may be provided with a flat swabable surface. In some embodiments, needle-free connector 102 may be provided with one or more antimicrobial features such as a chlorhexidine-eluting antimicrobial feature implemented as an insert ring, a coating or a lubricant at one or more locations within a chamber of the valve.

Needle-free connector 102 provides multiple access ports for continuous and intermittent infusion in a compact size with a positive, negative, or neutral displacement needle-free connector having a planar swabable surface for ease of cleaning. In various embodiments, any or all of ports 104, 106, and/or 108 can be directly attached to a syringe or tubing or may have a threaded connection at an outer end for, for example, connecting to threaded female Luer adapters.

Figure 2:
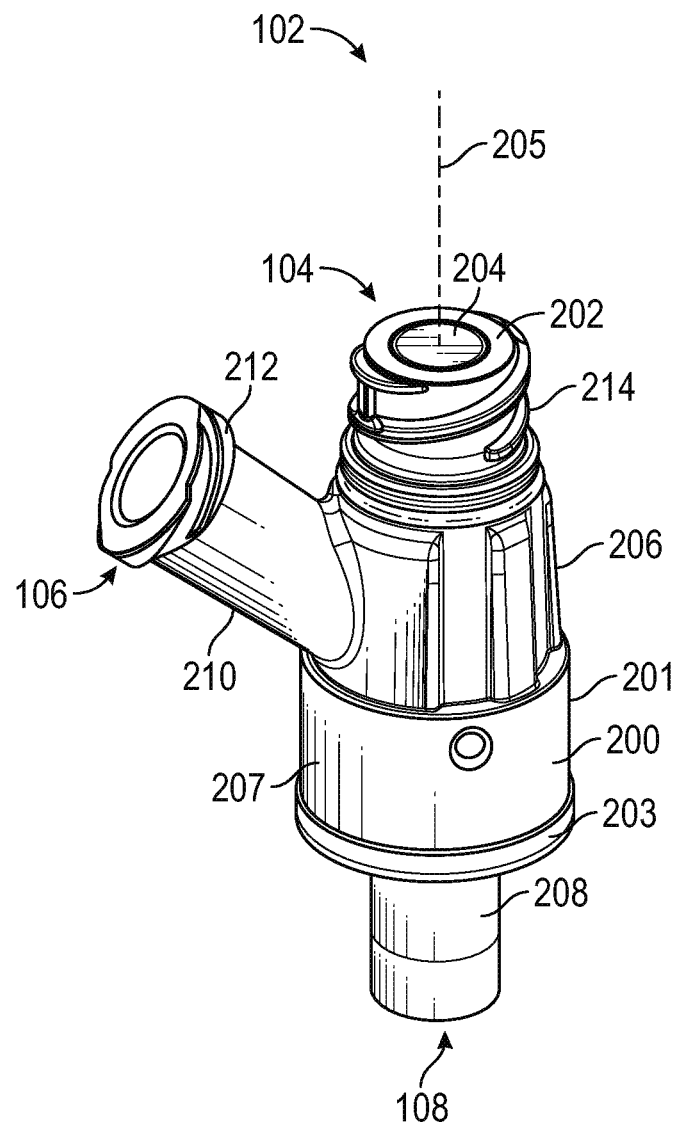
FIG. 2 illustrates an example of a needle-free connector, in accordance with aspects of the present disclosure.

FIG. 2 shows a perspective view of a needle-free connector with multiple input ports according to an embodiment. As shown in FIG. 2, needle-free connector 102 may include a positive displacement needle-free connector input port 104 and an open y-port 106 in a housing 200. Housing 200 may be a monolithic housing structure or may include an upper housing 201 and a lower housing 203 that enclose an internal chamber within which valve member 204 (e.g., a compressible silicon sealing member) is disposed.

As shown in FIG. 2, upper housing 201 may include an elongate main structure 207 (sometimes referred to herein as a central elongate portion) that extends along a longitudinal axis 205. Second input port 106 may be formed from an extension 210 of housing 200 that extends from a sidewall of the elongate main structure 207 at a non-parallel angle to the longitudinal axis. Second input port 106 allows a secondary access port into the fluid path between the upper housing 201 and valve member 204 for fluid administration or aspiration (i.e., drawing blood or fluid) while the needle-free valve 104 is closed (e.g., un-connected to a fluid source such as an IV bag or a syringe) or open (e.g., connected a fluid source such as an IV bag or a syringe).

In various embodiments, needle-free valve 104 may be a positive displacement valve, a neutral displacement valve, or a negative displacement valve. Valve member 204 may be a collapsible internal valve member made of a flexible material. When a force is applied to the top of the valve member 204 (e.g.; by the tip of a male Luer connector (not shown)), the valve may fold or otherwise compress or open, thereby opening a flow path through the connector 102. In the closed position (i.e., an uncompressed state for valve member 204) shown in FIG. 2, a seal may be formed between, for example, a shoulder of the valve and a sealing ridge of the housing 200 and or between a rim around the external surface of the valve member 204 and the edge of the opening in top surface 202 of housing 200.

Although the embodiment shown in FIG. 2 shows first input port 104 implemented as a needle-free valve and second input port 106 implemented as an open Luer access port, this is merely illustrative and either or both of input ports 104 and 106 can be implemented as a needle-free valve, an open Luer port, or other needle-free connector.

Output port 108 may be formed from a hollow cylindrical bottom extension 208 that extends, for example, along the longitudinal axis defined by main structure 207 of upper housing 201. Extension 208 may be an extended portion of lower housing structure 203 that is configured to form a tubing attachment for connector 102. Features such as ribs 206 on housing 200 may have corresponding internal features that help form a chamber that guides the motion of valve member 204 when the valve is compressed to form a continuous fluid pathway from input 106 to output 108.

Additional internal features such as standoff structures may be formed at or near extension 210 to prevent compression of valve member 204 from blocking or obstructing a fluid path from input 106 to output 108 as discussed in further detail herein after (see, for example, FIG. 13). Such standoff features may help ensure the y-port fluid path remains open when the needle-free connector port is accessed and the valve is collapsed. Threads 212 and 214 may be formed on an outer surface (or inner surface) of upper housing 201, respectively at inputs 106 and 104 to form threaded ports for connection to a fluid source or receptacle (e.g., an IV bag or a syringe).

Figure 3:
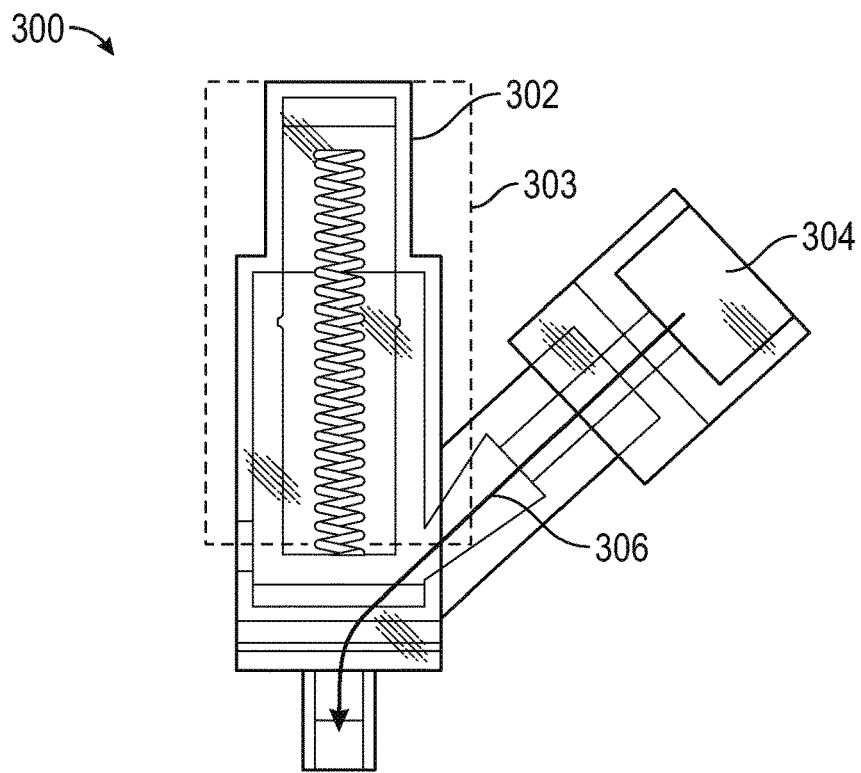
FIG. 3 illustrates a conventional connector.
Figure 4:
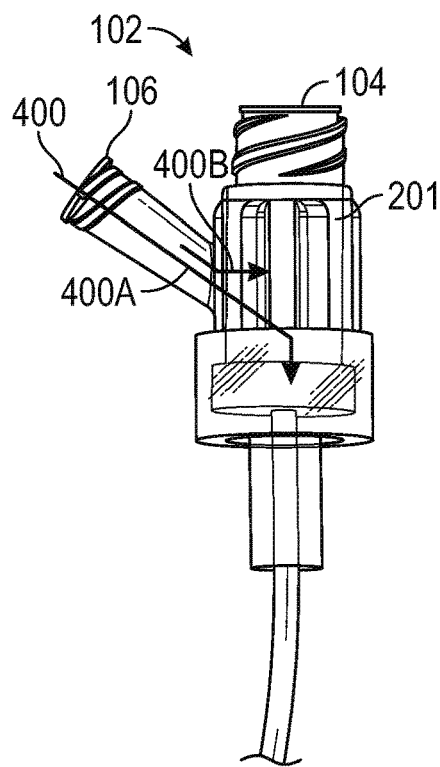
FIG. 4 illustrates an example of a fluid path of a needle-free connector, in accordance with aspects of the present disclosure.

As shown in FIG. 4, an open port 106 that accesses the connector 102 at a sidewall portion of the upper housing 201 allows for a compact length and maximum flushability compared to conventional mechanical valves (see FIG. 3 showing a conventional valve 300 having an additional port 304 with fluid path 306 entering distally to the valve components 302 thereby creating a relatively more complex internal fluid geometry that prevents adequate flushing in a non-flushable area 303 from fluid path 306 and can therefore significantly increase the risk of microbial colonization). As shown in FIG. 4, y-port 106 may access connector 102 through the upper housing 201, which may provide a fluid path 400 including internal chamber paths 400A and 400B that improve flushability of the connector and therefore reduce the risk of microbial colonization.

Figure 5:
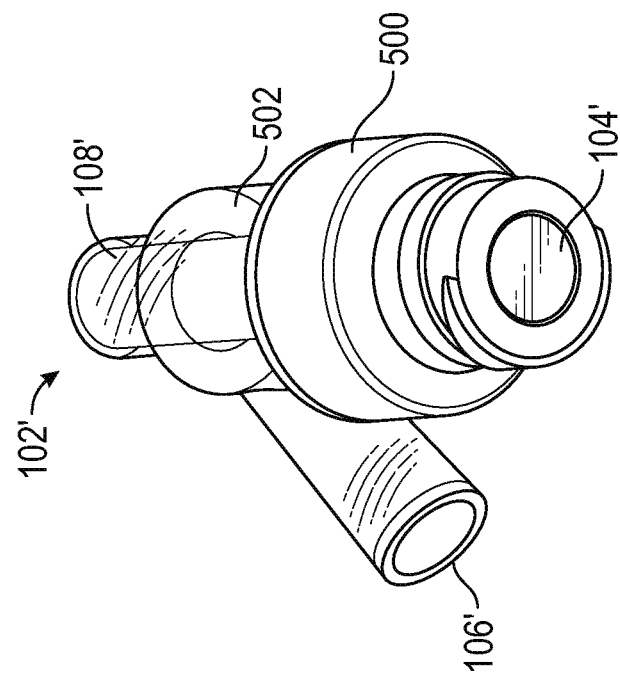
FIG. 5 illustrates a perspective view of examples of needle-free connectors having a first input port implemented as a positive displacement needle-free valve and a negative-displacement needle-free valve, in accordance with aspects of the present disclosure.
Figure 5:
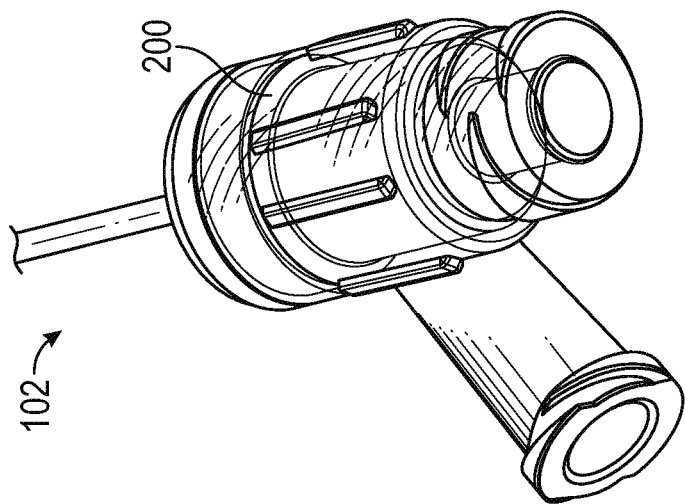

FIG. 5 illustrates perspective views of connector 102 (left with a positive displacement valve 104 and another embodiment of the connector 102' with a negative displacement needle-free valve 104'. As shown in FIG. 5, connector 102 at the left of the figure has a the y-port access in the upper housing as in FIGS. 1, 2, and 4 and connector 102' at the right of the figure includes a y-port access 106' at a lower housing structure 502, Lower housing structure 502 may engage with or otherwise be attached to an upper housing 500 that encloses the compressible negative displacement valve 104', Lower housing 502 may include an output port 108' along a longitudinal axis of the lower housing.

Figure 6:
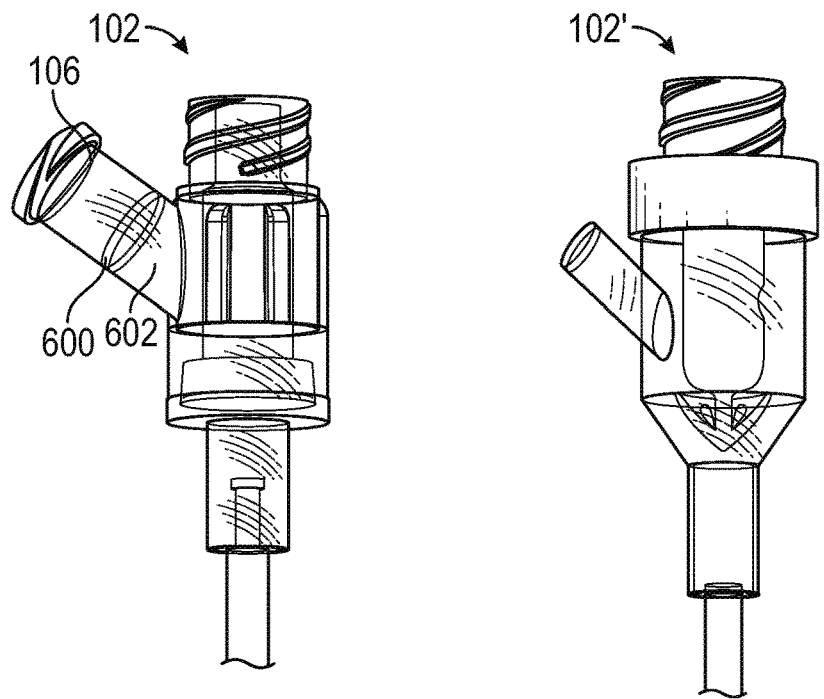
FIG. 6 illustrates a side view of the needle-free connectors of FIG. 5, in accordance with aspects of the present disclosure.

FIG. 6 shows side views of connectors 102 and 102' of FIG. 5. As shown in FIG. 6, Luer access y-port 106 may include an antimicrobial eluting insert or coating 600 at the distal end 602 of the Luer opening to provide a further reduction of microbial colonization risk. Antimicrobial eluting coatings, rings, and/or lubricants can be included at other internal locations such as a lower portion of the housing (e.g., surrounding output port 108) and/or on and/or around the compressible internal sealing member (e.g., an antimicrobial eluting lubricant on the valve 104 or a portion of the housing along which the valve travels when compressed and/or released). In some embodiments, one or more of valve 104 and port 106 may include features of a mechanical valve (e.g., one or more o-rings, a piston, a piston chamber, one or more gaskets, one or more springs, etc.). In these embodiments, antimicrobial eluting features may be disposed on or around one or more o-rings (e.g., on or around an upper o-ring and a lower o-ring of the valve), on or around a piston, on or around a piston chamber, on or around one or more gaskets, and/or on or around one or more springs.

Antimicrobial eluting features may elute a substance when a fluid contacts the features e.g., chlorhexidine, octenidine, silver, and/or other antimicrobial agents may be eluted). An antimicrobial eluting feature may be implemented as any of an antimicrobial eluting ring, a coating, or a lubricant. Connector 102' or other connector implementations described herein may also be provided with one or more antimicrobial eluting coatings, ring inserts or lubricants. Examples of antimicrobial features that can be provided in the needle-free connectors described herein are described in U.S. Patent Publication No. 2015/0231307, U.S. Pat. Nos. 8,426,348 and 8,754,020, and U.S. patent application Ser. No. 12/397,760, all of which are hereby incorporated by reference herein in their entireties.

Figure 7:
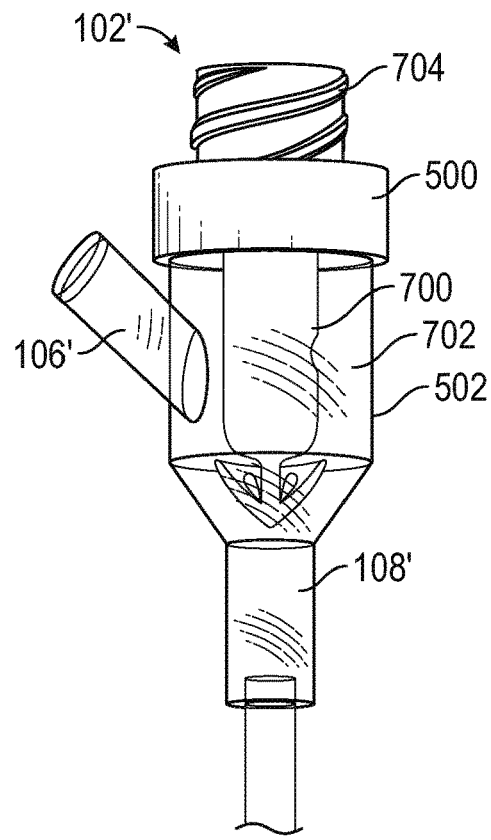
FIG. 7 illustrates an enlarged perspective view of the negative-displacement needle-free valve of FIG. 5, in accordance with aspects of the present disclosure.

FIG. 7 shows an enlarged perspective view of needle-free connector 102' showing how a negative displacement needle-free valve 700 may be provided between upper housing 500 and lower housing 502 within chamber 702. As shown, upper housing 500 may include threaded features 704 for coupling to a source such as IV tubing or a syringe. As shown, second input port 106' extends from a sidewall of a central elongate portion of lower housing 502 to provide access to the chamber 702.

Figure 8:
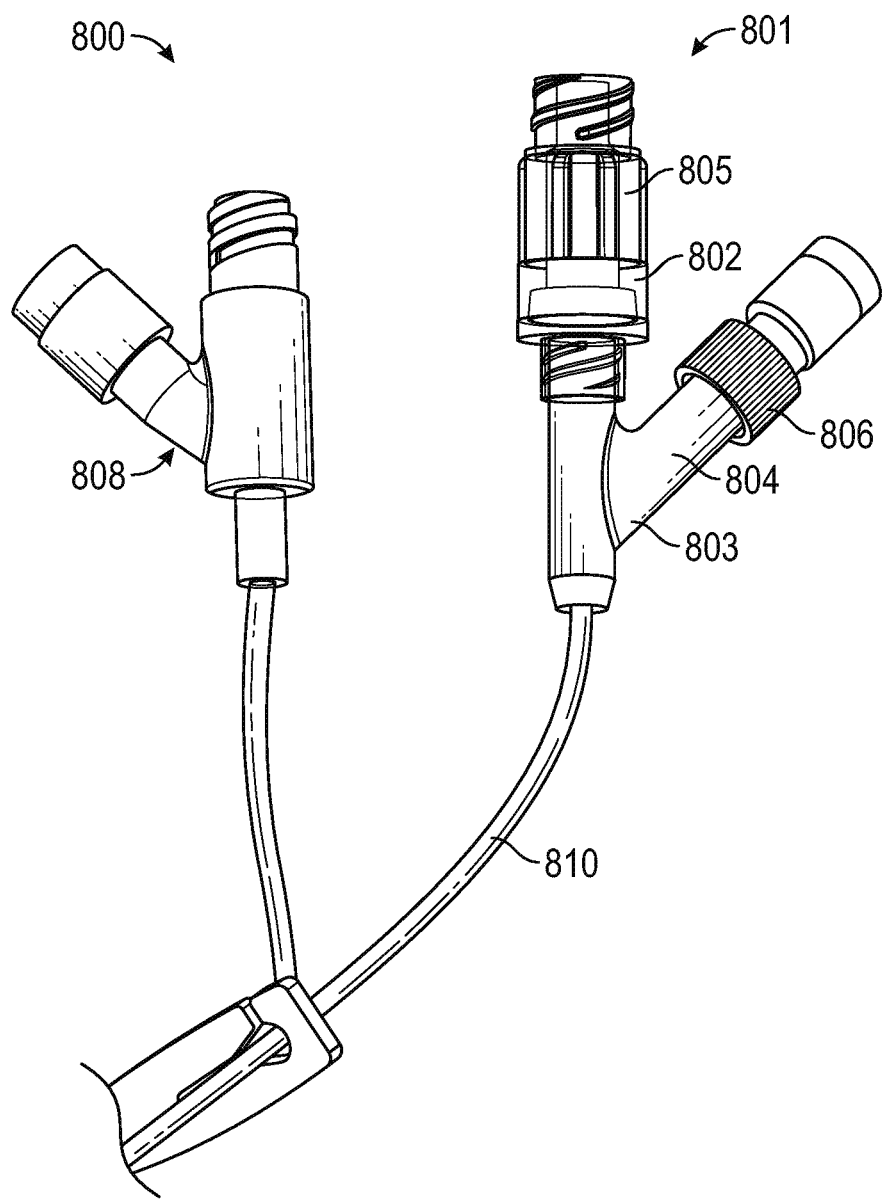
FIG. 8 illustrates a perspective view of an example of a system having multiple needle-free connectors, in accordance with aspects of the present disclosure.

FIG. 8 shows an example of a system 800 having a multiple connectors 801 and 808. As shown, connector 801 may include a positive displacement needle-free valve 805 with a housing 802 that engages with a lower housing 803 having a y-port 804 such that the output of the needle-free valve 805 feeds into lower housing 803 to join with a fluid path from y-port 804 to couple to tubing 810, A removable end cap 806 is shown that seals y-port 804 when installed at the open end of the y-port.

Figure 9:
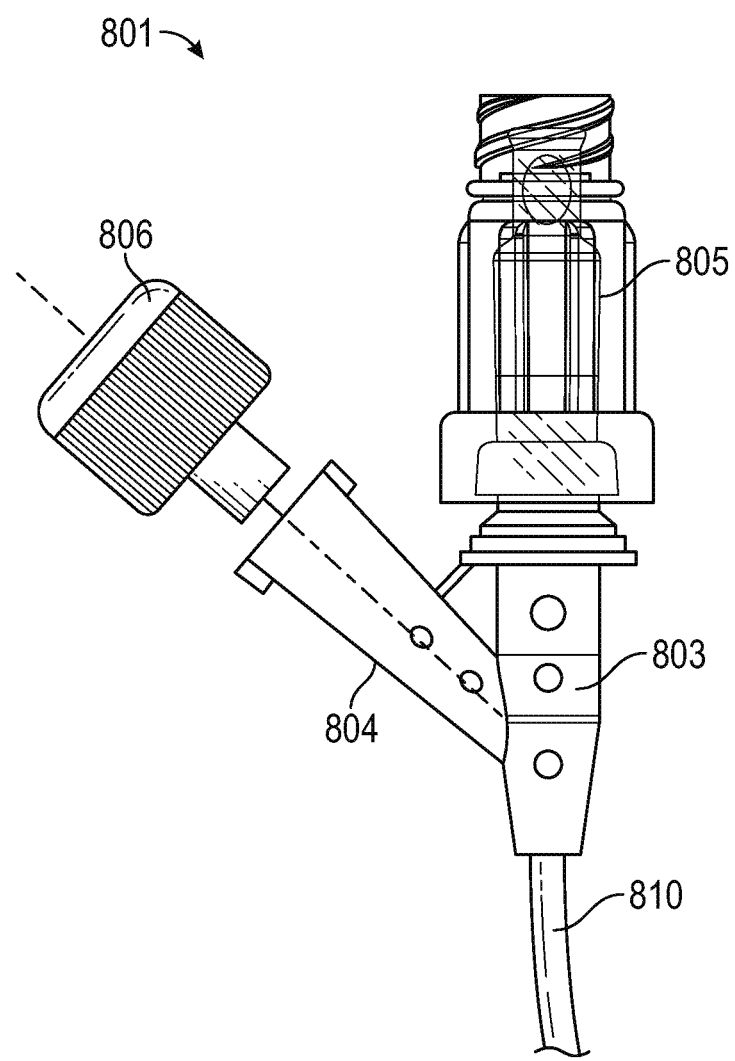
FIG. 9 illustrates a side view of one of the needle-free connectors of FIG. 8, in accordance with aspects of the present disclosure.

FIG. 9 shows a side view of connector 801 of FIG. 8 with end cap 806 disengaged from y-port 804 (e.g., to allow connection of a syringe to the y-port).

Figure 10:
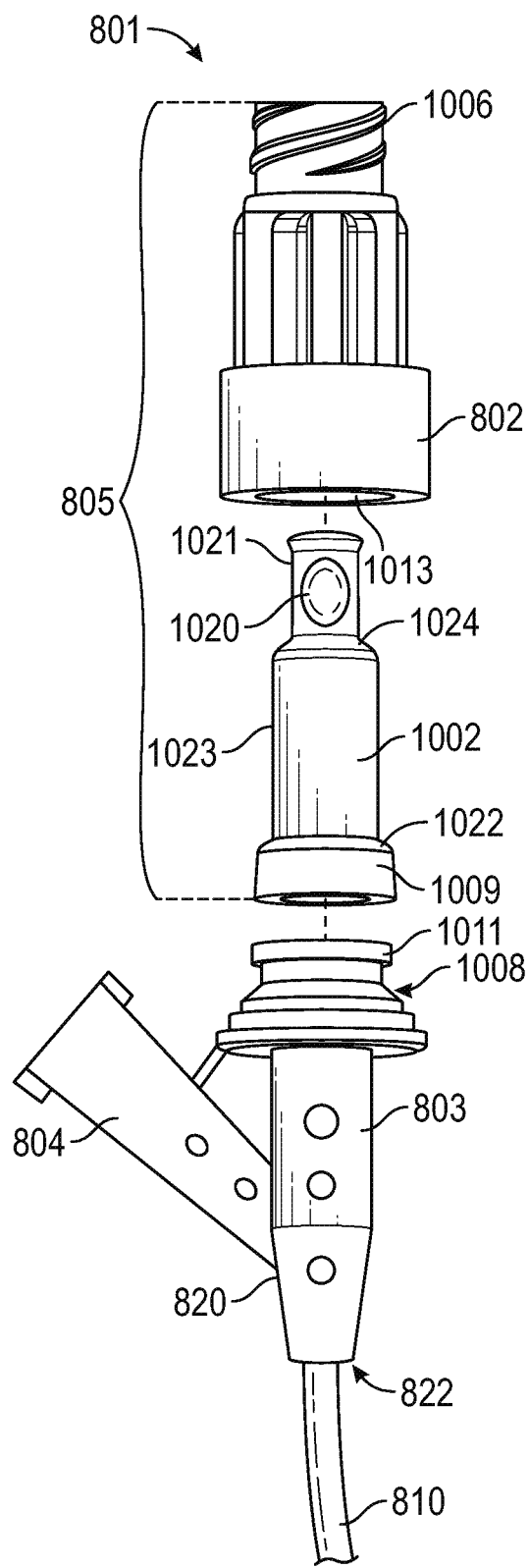
FIG. 10 shows an exploded side view of the connector of FIG. in accordance with aspects of the present disclosure.

FIG. 10 shows an exploded side view of connector 801 of FIG. 8 showing how a compressible sealing member 1002 may be disposed between upper housing 802 and lower housing 803 to form the needle-free valve 805. Engagement features 1008 on lower housing 803 are visible that engage with corresponding internal features of upper housing 802 to seal valve member 1002 within the chamber formed within the housing structures and/or that provide a fluid path around portions of member 1002 to an output port within lower housing 803, Threaded features 1006 are also shown on an outer surface of upper housing 802.

In this way, a needle-free connector 801 is provided that includes a lower housing 803 having a sidewall 820, a needle-free valve 805 that includes upper housing 802 and compressible sealing member 1002 disposed between the upper housing 802 and the lower housing 803, a y-port 804 formed from a portion of the lower housing that extends at a non-parallel angle from the sidewall 820 of the lower housing 803, and an output port 822 in the lower housing 803, the output port fluidly coupled to the needle-free valve 805 and the y-port 804. Lower housing 803 may include one or more openings (not visible in FIG. 10) that allow fluid that flows past compressible sealing member 1002 within upper housing 802 to pass into lower housing 803 and to output port 822.

Compressible sealing member 1002 may include a circumferential flange 1009. Engagement features 1008 of lower housing 803 may include an engagement feature 1011 (e.g., a lip) that secures the circumferential flange 1009 between the engagement feature 1011 and a portion of the interior surface 1013 of the upper housing 802. For example, circumferential flange 1009 may have a shoulder 1022. Shoulder 1022 have a shape that corresponds to the shape of a portion of interior surface 1013 as described in further detail hereinafter.

As shown in FIG. 10, compressible sealing member 1002 may include one or more features that facilitate and guide compression of member 1002 such as a notch 1020 in a neck portion 1021. Neck portion 1021 may extend from a relatively wider central cylindrical portion 1023 disposed between neck portion 1021 and flange 1009. An upper shoulder 1024 may be formed between central cylindrical portion 1023 and neck portion 1021. Shoulder 1022 may be a lower shoulder that is formed between central cylindrical portion 1023 and flange 1009.

Figure 11:
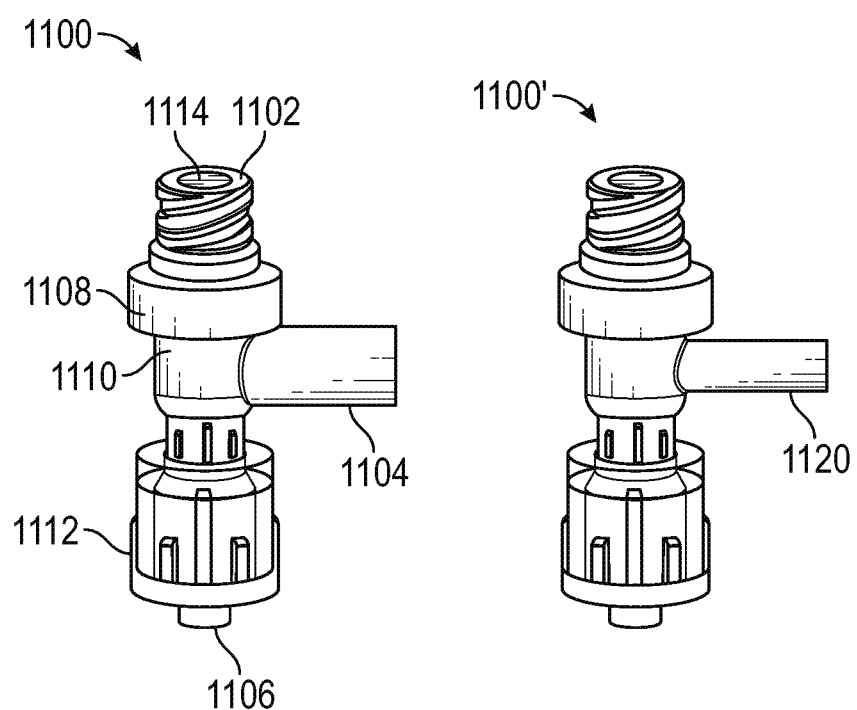
FIG. 11 shows two additional embodiments of a needle-free connector having first and second input ports and an output port, in accordance with aspects of the present disclosure.

FIG. 11 shows two additional embodiments of a needle-free connector having first and second input ports and an output port. In the example on the left of FIG. 11, needle-free connector 1100 includes a first input port 1102, a perpendicular second input port 1104, and an output port 1106. Connector 1100 includes an upper housing 1108, a lower housing 1110, and a valve (e.g., a compressible sealing member) 1114 that forms a needle-free valve that is perpendicular to second input port (e.g., an open Luer port) 1104. A coupling member 1112 is formed on lower housing 1110 for engaging output port 1106 with, for example, tubing or another output container, Connector 1100' at the right of FIG. 11 shows how a relatively narrower second input port 1120 may be provided.

Figure 12:
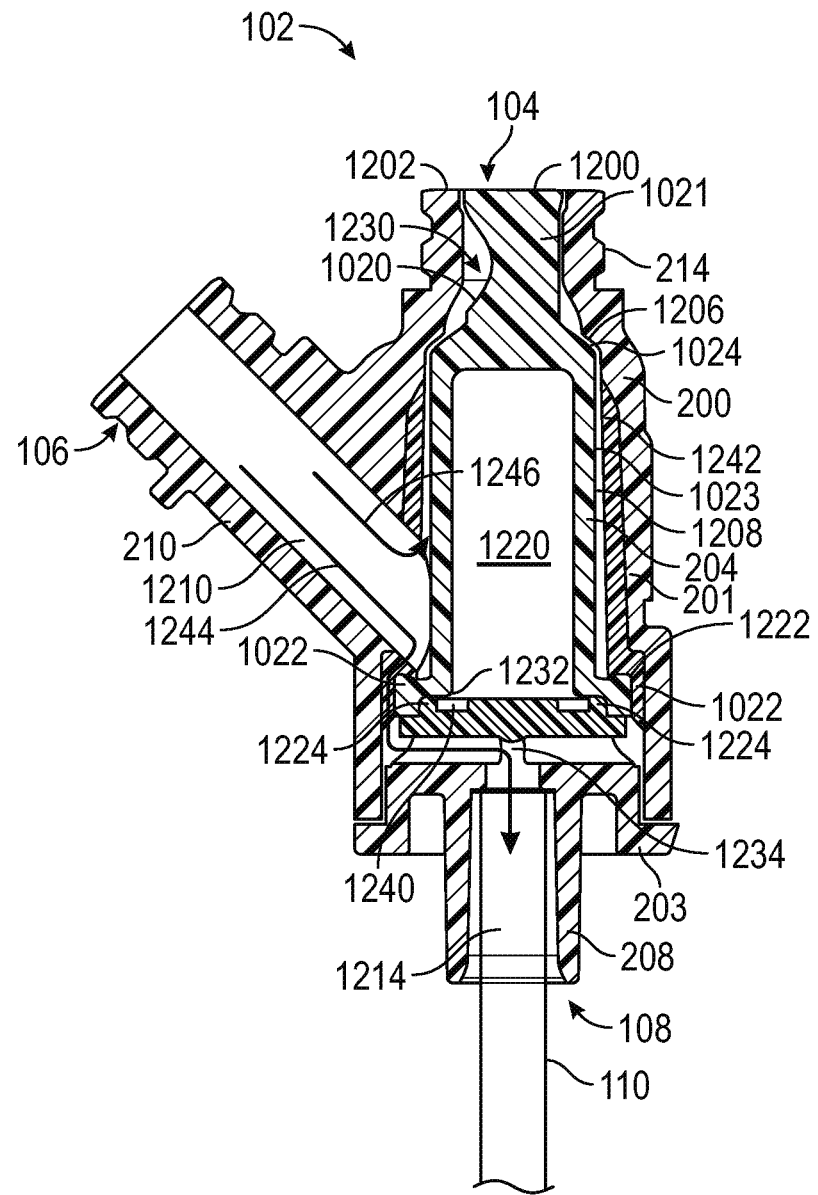
FIG. 12 shows a cross-sectional view of a needle-free connector, in accordance with aspects of the present disclosure.

FIG. 12 shows a cross-sectional view of connector 102 according to an embodiment. In the example of FIG. 12, valve member 204 is disposed within a chamber 1208 within upper housing 201 and enclosed by upper housing 201 and lower housing 203. An internal bore 1210 in y-port 106 is shown fluidly connected to chamber 1208. Lower housing 203 also includes an internal bore 1214 for receiving tubing 110. Valve member 204 may include features such as a shoulder 1024 that engages with a recess 1206 in the chamber 1208 to help seal needle-free valve 104 when compressible sealing member 204 is in the uncompressed state shown in FIG. 12. When pressed at top surface 1200, compressible sealing member 204 may be deformed to a compressed state that allows fluid to flow between valve 104 and output port 108. Valve member 204 may include one or more features such as cutout 1020 in compressible sealing member 204 that forms a cavity 1230 within valve 104 that ensures that a desired fluid path is formed when the valve is in the compressed state.

As shown in FIG. 12, compressible sealing member 204 may include a central cavity 1220 that helps provide flexibility for compression. FIG. 12 shows how, in the uncompressed state, top surface 1200 of compressible sealing member 204 may form a planar surface in a common plane with the top surface 1202 of upper housing 201. In this way, a flat (planar), swabable surface may be provided that is easily cleaned before and/or after use.

FIG. 12 also shows how shoulder 1022 may conform to a recess 1222 in a portion of the inner surface of housing 201. An inner portion of flange 1009 may also interface with a protrusion 1224 of lower housing 203 to help secure compressible sealing member 204 between upper housing 201 and lower housing 203. A recess 1240 may be provided in lower housing 203 into which an inner shoulder 1232 of compressible sealing member 204 can move during compression in some implementations.

As shown in FIG. 12, a cutout 1242 may be provided in the inner surface of upper housing 201 that enlarges, in some locations, the size of chamber 1208 within housing 201 so that a fluid path can be established between the input port of needle-free valve 104, through chamber 1208, through opening 1234 of lower housing 203, and to output port 108 when compressible sealing member 204 is compressed. As shown, y-port 106 may provide a fluid path 1246 into chamber 1208 whether or not sealing member 204 is compressed. In this way, a chamber 1208 is provided within housing 201 that can be flushed via port 106 or port 104, if desired. A fluid flow path 1244 may also be provided from port 106 through opening 1234 to output port 108. Fluid flow path 1246 may be a portion of fluid flow path 1244 that flows into and within chamber 1208 prior to flowing out of output port 108.

The configuration of valve 104 shown in FIG. 12 is merely illustrative and other implementations of a needle-free valve may be used in combination with a y-port that feeds a common chamber with the needle-free valve, Various examples of needle-free valve configurations are described in U.S. patent application Ser. Nos. 13/801,399, 13/801,412, and 13/801,422, all of which are hereby incorporated by reference herein in their entireties.

Figure 13:
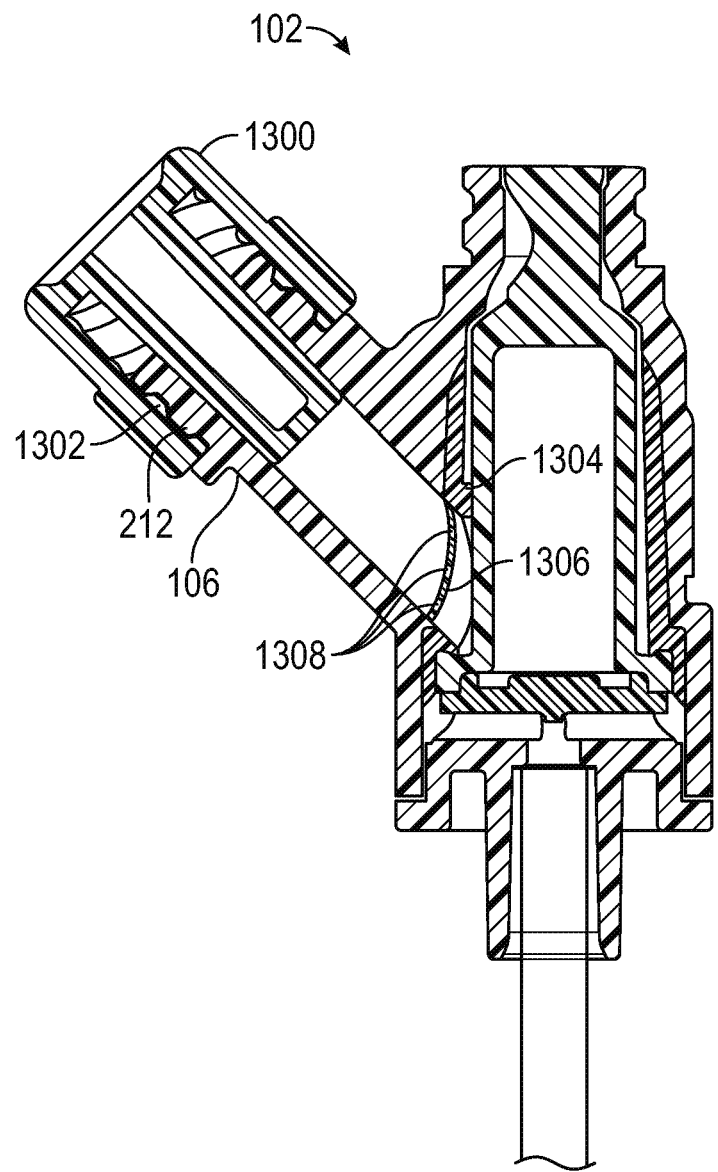
FIG. 13 shows a cross-sectional view of the connector of FIG. 12 with an end cap on a y-port of the connector, in accordance with aspects of the present disclosure.

FIG. 13 shows a cross-sectional view of the connector 102 of FIG. 12 with an end cap 1300 engaged on y-port connector 106 via engagement between threaded features 1302 on end cap 1300 and corresponding threaded features 212 on y-port 106. FIG. 13 also shows optional features such standoff features 1304 and 1306 that may be provided to prevent compressible sealing member 204 from blocking port 106 in a compressed configuration. For example, standoff feature 1304 may be a protrusion from an inner wall of upper housing 201, the protrusion extending into chamber 1208 to block and/or guide movement of compressible sealing member 204 during compression. As another example, standoff feature 1306 may be a porous screen having openings 1308 to allow fluid flow therethrough. Screen 1306 may extend from port 106 into chamber 1208 to block and/or guide movement of compressible sealing member 204 during compression.

Figure 14:
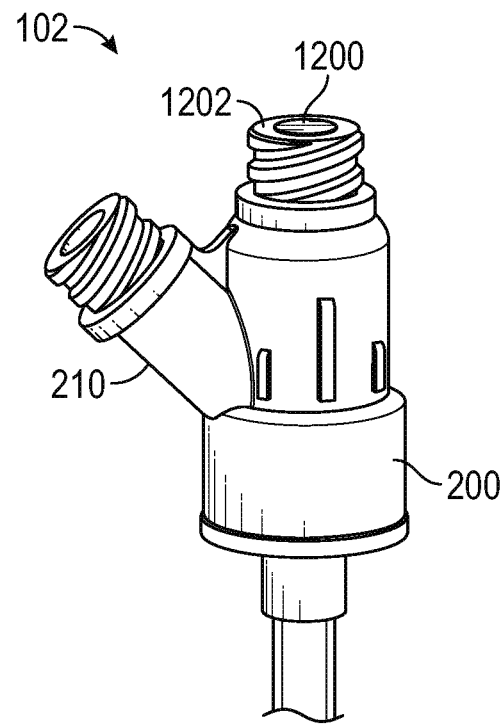
FIG. 14 illustrates a perspective view of the connector of FIG. 12, in accordance with aspects of the present disclosure.
Figure 15:
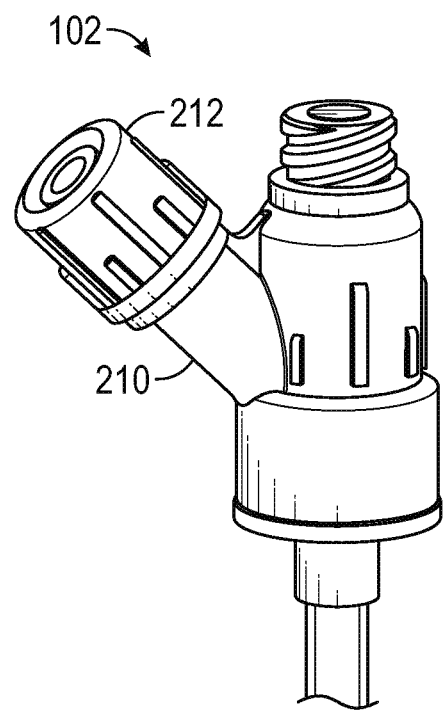
FIG. 15 shows a perspective view of the connector of FIG. 13, in accordance with aspects of the present disclosure.

FIG. 14 is a perspective view of connector 102 showing the planar, flat swabable surface formed from top surface 1200 of valve member 204 and top surface 1202 of housing 200. FIG. 15 shows a perspective view of the connector 102 of FIG. 14 with an end cap 1300 engaged on y-port connector 106 (e.g., on extension 210).

Figure 16:
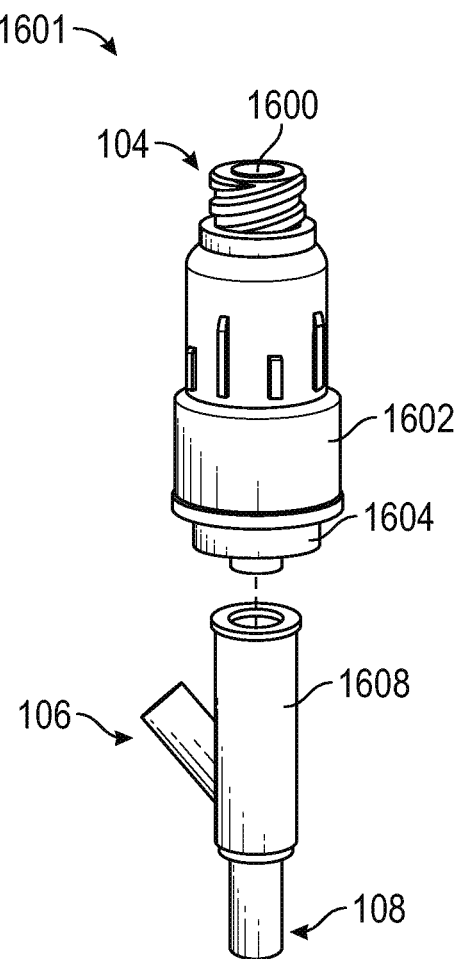
FIG. 16 illustrates an exploded perspective view of a needle-free connector having an upper housing, an intermediate housing, and a lower housing with a y-port, in accordance with aspects of the present disclosure.
Figure 17:
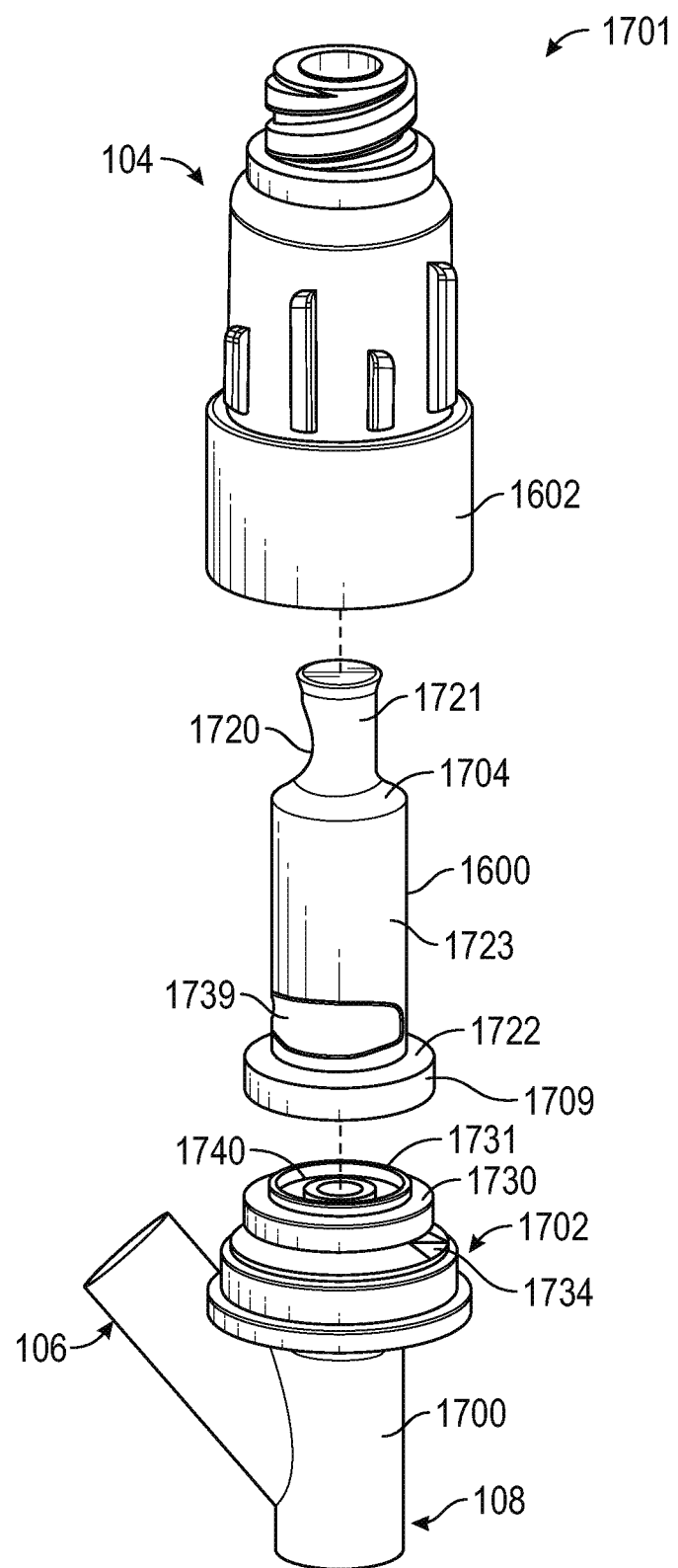
FIG. 17 illustrates an exploded perspective view of a needle-free connector having an upper housing, and a lower housing with a y-port, in accordance with aspects of the present disclosure.
Figure 18:
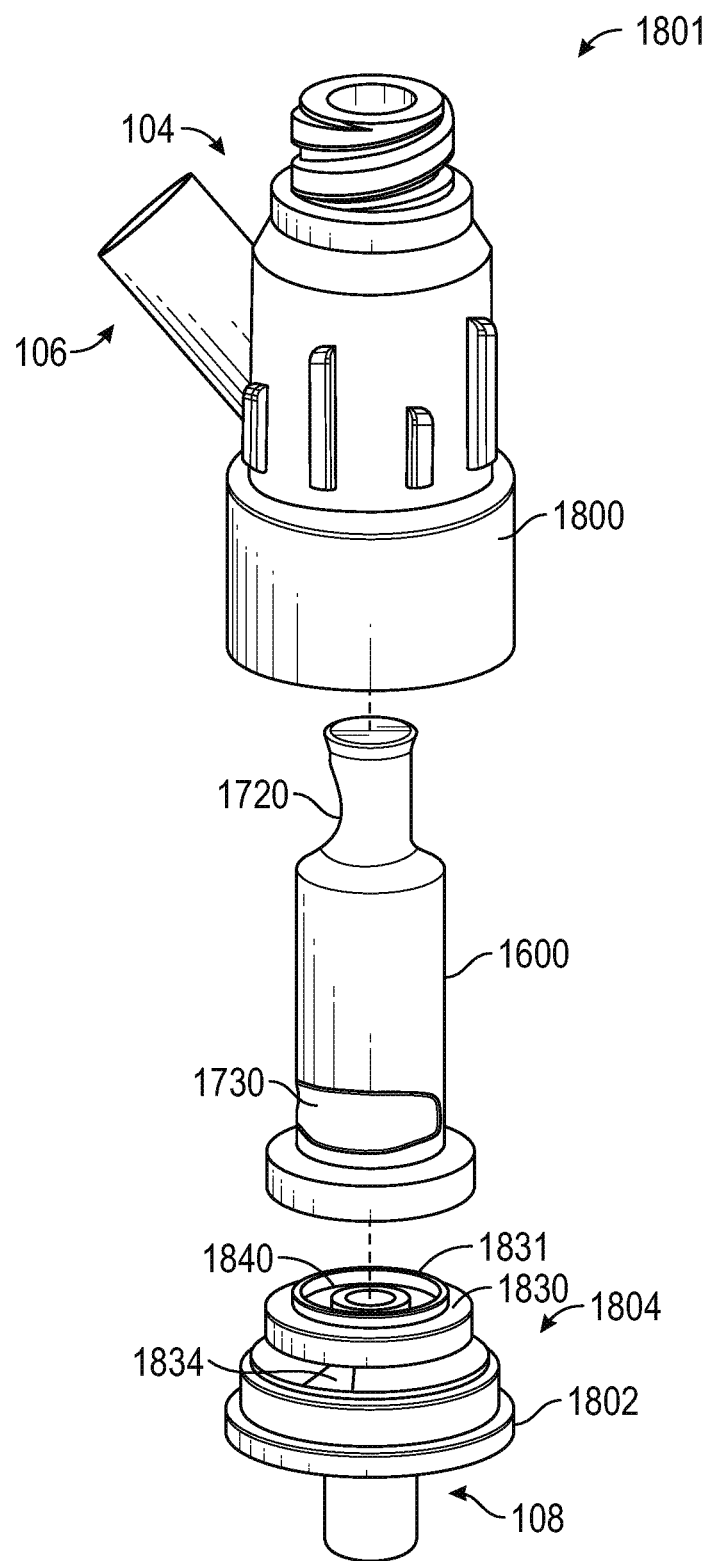
FIG. 18 illustrates an exploded perspective view of a needle-free connector having an upper housing with a y-port and a lower housing, in accordance with aspects of the present disclosure.

FIGS. 16, 17, and 18 show exploded perspective views of several respective embodiments of a needle-free connector having a needle-free valve and a y-port according to various embodiments. In the example of FIG. 16, needle-free connector 1601 includes (a) a needle-free valve 104 formed from an upper housing 1602, a compressible sealing member 1600, and an intermediate housing 1604, (b) a y-port 106 formed in a lower housing 1608 configured to engage with intermediate housing 1604, and (c) an output port 108 in the lower housing 1608.

In the example of FIG. 17, needle-free connector 1701 includes (a) a needle-free valve 104 formed from an upper housing 1602, a compressible sealing member 1600, and a lower housing member 1700, (b) a y-port 106 formed in the lower housing 1700, the lower housing 1700 having engagement features 1702 configured to engage with upper housing 1602 and/or compressible sealing member 1600, and (c) an output port 108 in the lower housing 1700.

As shown in FIG. 17, compressible sealing member 1600 may include a circumferential flange 1709 having a shoulder 1722. Shoulder 1722 may have a shape that corresponds to the shape of a portion of an interior surface of upper housing 1602.

Compressible sealing member 1600 may include one or more features that facilitate and guide compression of member 1600 such as a notch 1720 in a neck portion 1721 and/or a notch 1739 in a cylindrical central portion 1723. Neck portion 1721 may extend from central cylindrical portion 1723. Central cylindrical portion 1723 may be disposed between neck portion 1721 and flange 1709. An upper shoulder 1704 may be formed between central cylindrical portion 1723 and neck portion 1721. Shoulder 1722 may be a lower shoulder that is formed between central cylindrical portion 1723 and flange 1709.

In the implementation of FIG. 17, lower housing 1700 includes a circular protrusion 1731 that forms a circular recess 1740 interior to circular protrusion 1731. An inner surface of flange 1709 may interface with an upper surface 1730, protrusion 1731, and recess 1740 in a similar manner to that described above in connection with protrusion 1224 and recess 1240 of FIG. 12 in some implementations. Fluid may flow from upper housing 1602 into lower housing 1700 to output port 108 via opening 1734 in lower housing 1730.

In the example of FIG. 18, needle-free connector 1801 includes (a) a needle-free valve 104 formed from an upper housing 1800, a compressible sealing member 1600, and a lower housing member 1802, (b) a y-port 106 formed in the upper housing 1800, the lower housing 1802 having engagement features 1804 configured to engage with upper housing 1800, and (c) an output port 108 in the lower housing 1802.

In the implementation of FIG. 18, lower housing 1802 includes a circular protrusion 1831 that forms a circular recess 1840 interior to circular protrusion 1831. An inner surface of flange 1709 may interface with an upper surface 1830, protrusion 1831, and recess 1840 in a similar manner to that described above in connection with protrusion 1224 and recess 1240 of FIG. 12 in some implementations. For example, lower housing 1802 may be an implementation of lower housing 203 in which protrusion 1224 is implemented as circular protrusion 1831 and recess 1240 is implemented as a circular recess 1840. Fluid may flow from upper housing 1800 (e.g., from port 104 and/or port 106) into lower housing 1802 to output port 108 via opening 1834 in lower housing 1802.

Figure 19:
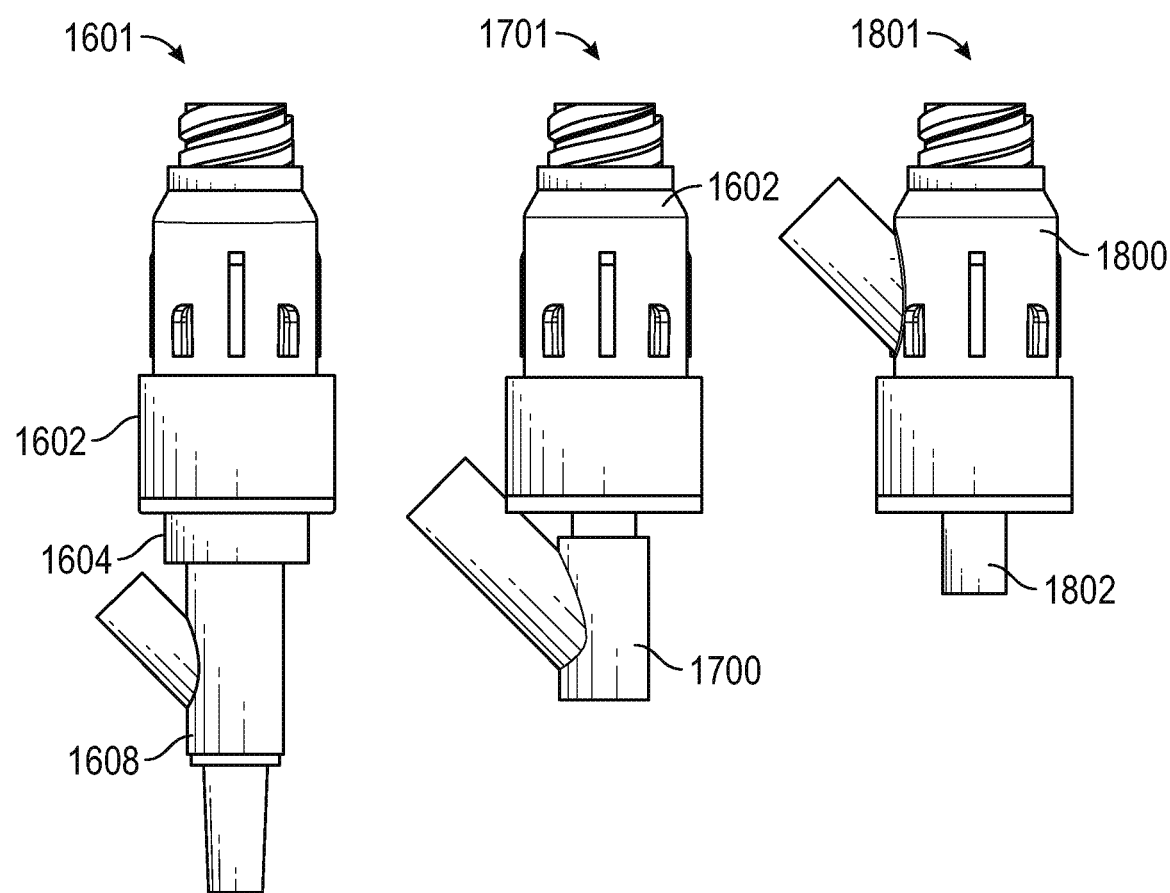
FIG. 19 illustrates side views of the connectors of FIGS. 16, 17, and 18, in accordance with aspects of the present disclosure.
Figure 20:
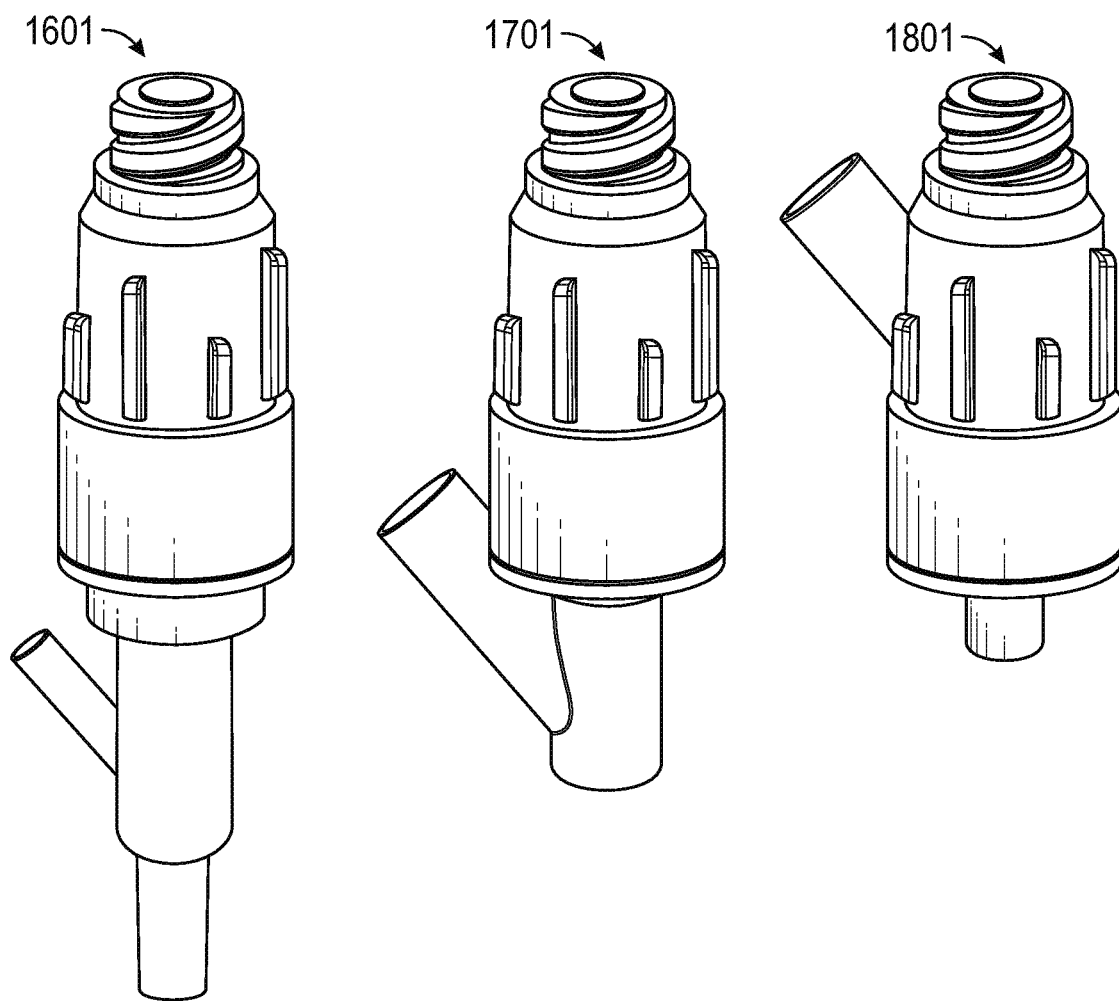
FIG. 20 illustrates perspective top views of the connectors of FIGS. 16, 17, and 18, in accordance with aspects of the present disclosure.
Figure 21:
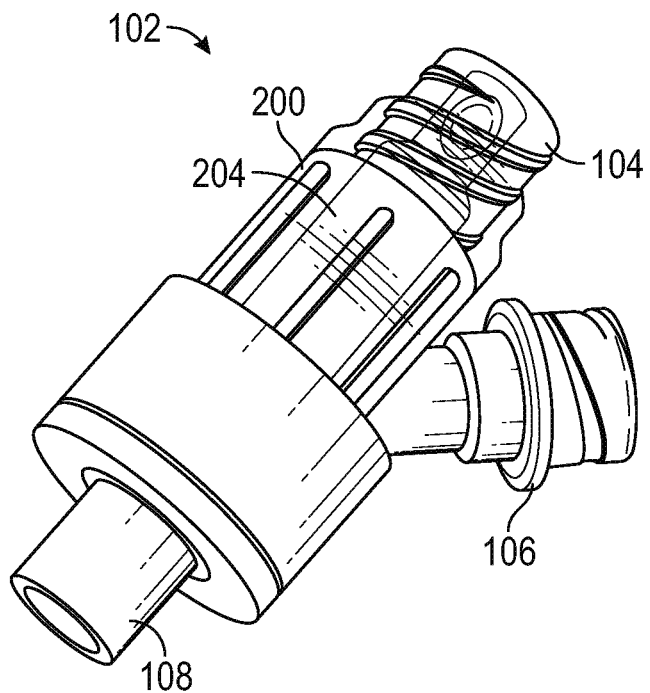
FIG. 21 illustrates a perspective bottom view of an example of a needle-free connector, in accordance with aspects of the present disclosure.
Figure 22:
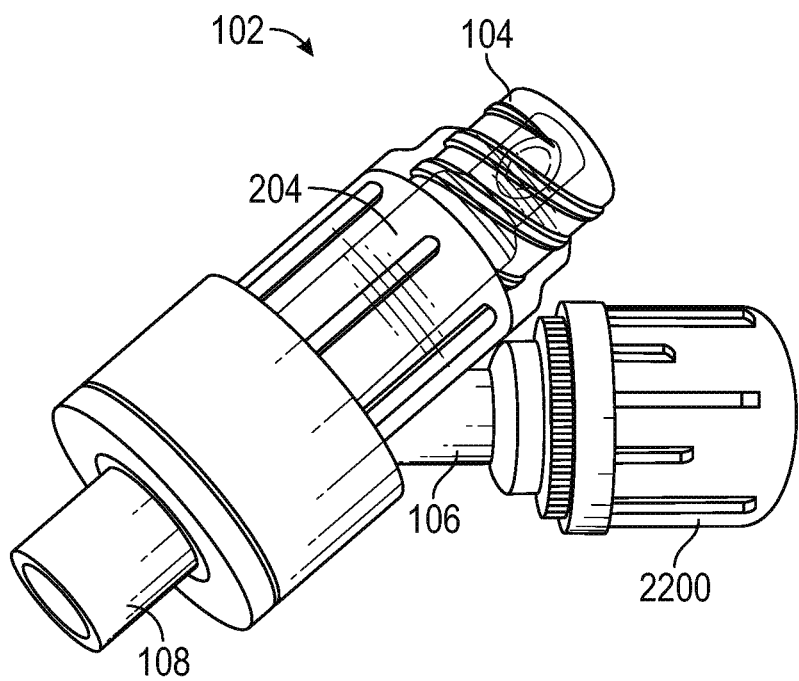
FIG. 22 illustrates a perspective bottom view of an example of a needle-free connector with an end cap on a y-port, in accordance with aspects of the present disclosure.
Figure 23:
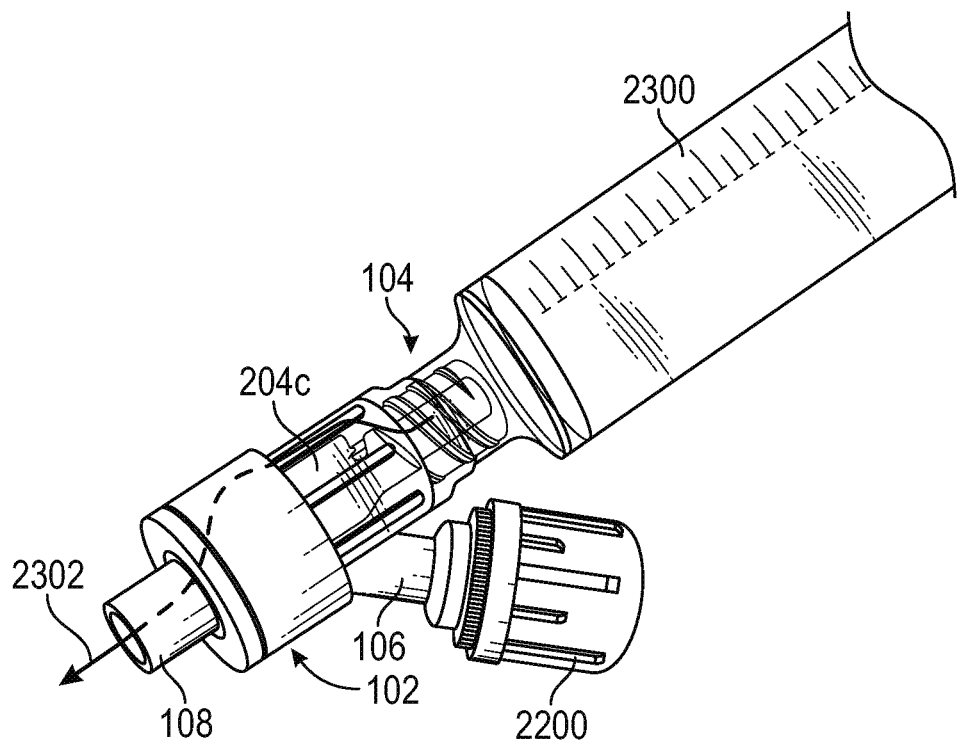
FIG. 23 illustrates a perspective view of an example of a needle-free connector with an end cap on a y-port and a needleless syringe attached to a needle-free valve, in accordance with aspects of the present disclosure.

FIG. 19 shows assembled side views of connectors 1601, 1701, and 1801 of FIGS. 16, 17, and 18. FIG. 20 shows assembled perspective top views of connectors 1601, 1701, and 1801 of FIGS. 16, 17, and 18 showing how each has a flat swabable surface formed by the top surface of the valve and the top surface of the upper housing FIG. 21 shows a perspective bottom view of the needle-free connector 102 of FIG. 2. FIG. 22 shows the needle-free connector 102 of FIG. 21 with an end cap 2200 sealingly engaged on second input port 106. FIG. 23 shows the needle-free connector 102 of FIG. 21 with an end cap 2200 sealingly engaged on second input port 106 and a needleless syringe 2300 attached to needle-free valve 104. As shown in FIG. 23, when a connector such as syringe 2300 is connected to needle-free valve 104, compressible sealing member 204 may be deformed to a compressed configuration 204C in which a fluid path 2302 is formed from needle-free valve 104 to output port 108.

Figure 24:
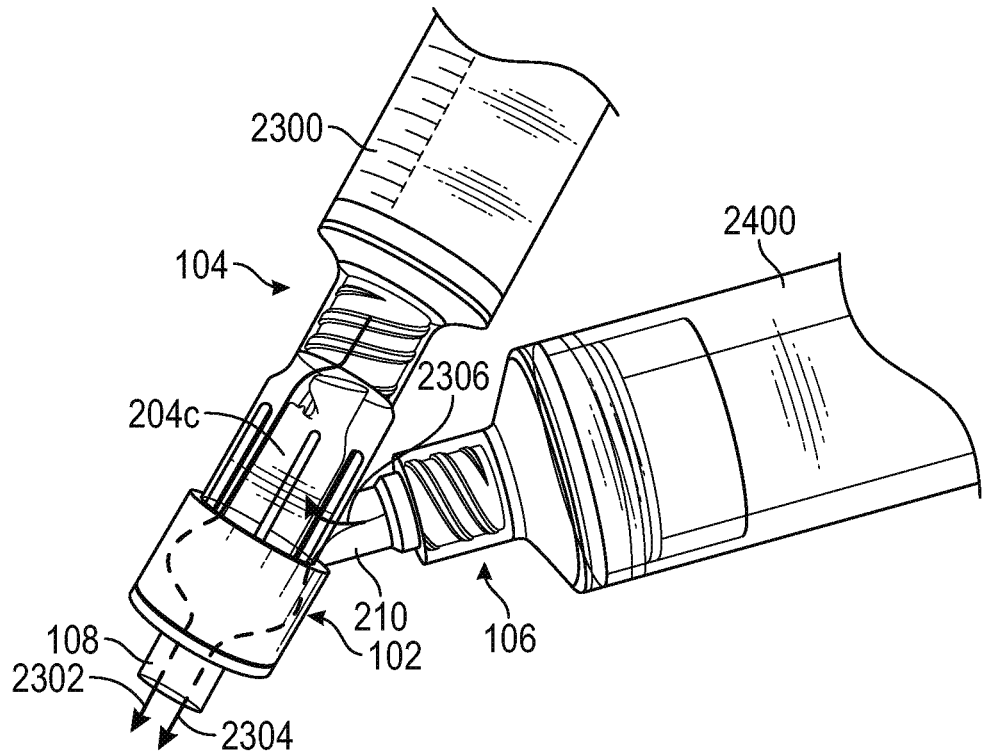
FIG. 24 illustrates a perspective view of an example of a needle-free connector with a first needleless syringe attached to a needle-free valve and a second needleless syringe attached to a y-port, in accordance with aspects of the present disclosure.

FIG. 24 shows the needle-free connector 102 of FIG. 21 with a first needleless syringe 2300 attached to needle-free valve 104 and a second needleless syringe 2400 attached to y-port 106. In a configuration such as that shown in FIG. 24, a first fluid may be provided from first syringe 2300 into a chamber (see, e.g., chamber 1208 of FIG. 12) within the connector via needle-free valve 104 along a first fluid path 2302 and a second fluid may be provided along fluid pathway 2306 into at least a portion of the same chamber from second syringe 2400 while the first and second syringes are both coupled to the needle-free connector 102. The second fluid from second syringe 2400 may also flow along a third fluid flow path 2304 from port 106 through output port 108. Some or all of the second fluid that flows into the chamber along fluid path 2306 may flush the chamber and may exit the chamber to flow out of output port 108. The first fluid from port 104 may also flush any remaining second fluid from the chamber after delivery of the fluid from port 106. The first and second fluids may be provided intermittently or in combination to a patient via output port 108.

Figure 25:
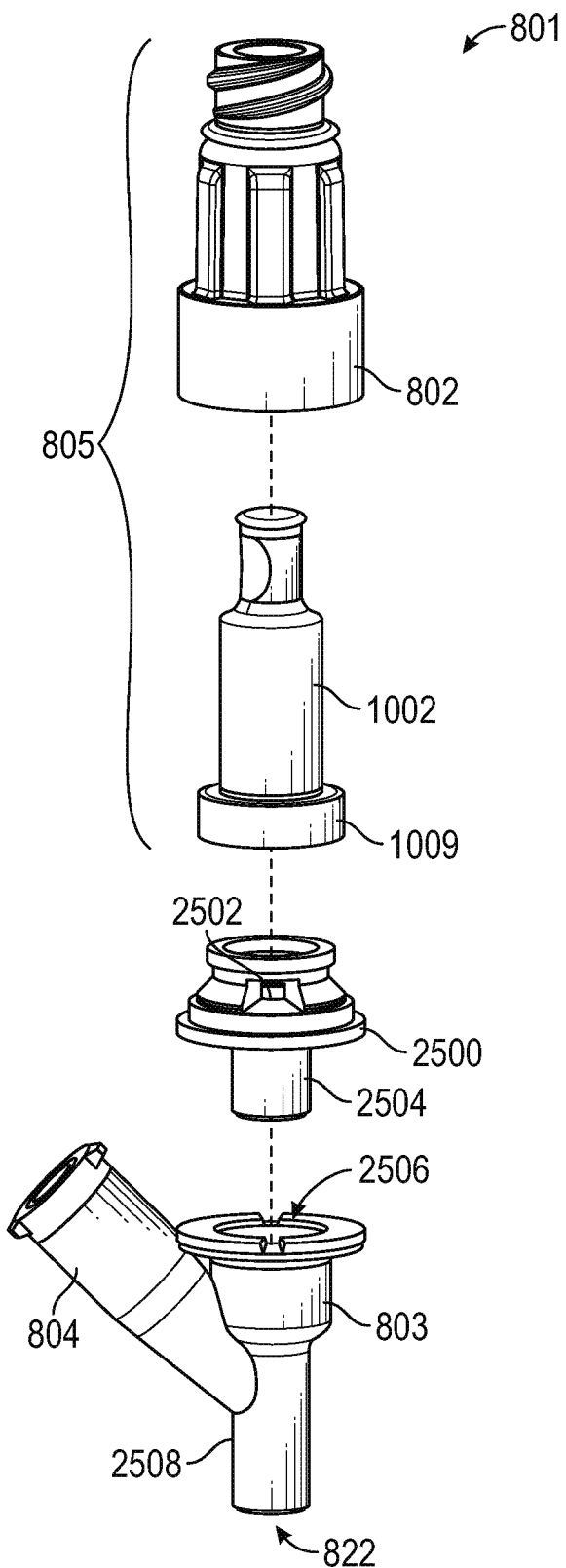
FIG. 25 shows an exploded side perspective view of an example of a needle-free connector having an upper housing, an intermediate housing, and a lower housing with a y-port, in accordance with aspects of the present disclosure.

FIG. 25 shows an exploded side perspective view of connector 801 implemented with an upper housing, a lower housing having a y-port, and an intermediate housing. As shown in FIG. 25, intermediate housing 2500 may be interposed between upper housing 802 and lower housing 803 such that flange 1009 interfaces with intermediate housing 2500 in an assembled configuration (see, e.g., FIG. 26). Intermediate housing 2500 may be provided with a central cylindrical extension 2504. Extension 2504 may have a central axis in common with the central axis of connector 801 and may extend into corresponding opening 2506 in lower housing 803 in an assembled configuration. Intermediate housing 2500 may include one or more openings such as opening 2502 through which fluid that flows past compressible sealing member 1002 within upper housing 802 can pass through opening 2502 into intermediate housing 2500, through extension 2504 into lower housing 803, and through output port 822. Intermediate housing 2500 may engage with internal features of upper housing 802 to seal valve member 1002 within a chamber formed by upper housing 802 and intermediate housing 2500.

In this way, a needle-free connector 801 is provided that includes a lower housing 803 having a sidewall 2508, a needle-free valve 805 that includes upper housing 802, intermediate housing 2500, compressible sealing member 1002 disposed between the upper housing 802 and intermediate housing 2500, a y-port 804 formed from a portion of the lower housing that extends at a non-parallel angle from the sidewall 2508 of the lower housing 803, and an output port 822 in the lower housing 803, the output port fluidly coupled to the needle-free valve 805 and the y-port 804.

Figure 26:
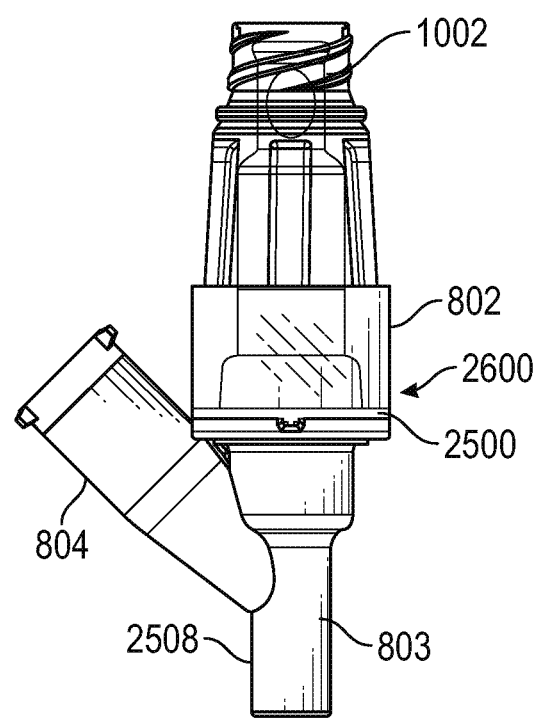
FIG. 26 shows a side view of the needle-free connector of FIG. 25 in an assembled configuration, in accordance with aspects of the present disclosure.

FIG. 26 shows an assembled side view of needle-free connector 801 of FIG. 25. As shown in FIG. 26, in the assembled configuration, an outer sidewall of connector 801 may be formed from portions of upper housing 802, intermediate housing 2500, and lower housing 803. For example, a portion of intermediate housing 2500 that forms a portion of sidewall 2600 may be interposed between a portion of lower housing 803, and a portion of upper housing 802 (e.g., to form a continuous cylindrical portion of sidewall 2600).

Needle-free connectors of the type described herein having a needle-free valve and liter access y-port may provide significant improvements in usability, compact form, ease of connection, ease of cleaning the connector valve surface, positive fluid displacement upon disconnect, and an additional benefit of antimicrobial efficacy. Needle-free connectors of the type described herein having a needle-free valve and Luer access y-port may provide all of the functionality of needle-free access with a secondary open access port in a form and configuration that reduces risk of microbial ingress, colonization, and blood reflux upon disconnection. The concepts described herein may also provide for flat and swabable surface for ease of cleaning prior to access to reduce the risk of introducing microbes into the system.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A needle-free connector, comprising:
 a housing;
 a first input port in the housing;
 a second input port in the housing;
 a chamber within the housing that is fluidly coupled to the first input port and the second input port; and
 an output port that is fluidly coupled to the chamber.

Concept 2. The needle-free connector of Concept 1 or any other Concept, further comprising a compressible sealing member within the housing, the compressible sealing member having an uncompressed state in which the compressible sealing member seals the first input port and a compressed state that allows a continuous fluid pathway between the first input port and the output port.

Concept 3. The needle-free connector of Concept 2 or any other Concept, wherein the continuous fluid pathway comprises a first continuous fluid pathway and wherein the needle-free connector further comprises a second continuous fluid pathway between the second input port and the output port.

Concept 4. The needle-free connector of Concept 3 or any other Concept; further comprising a third continuous fluid pathway from the second input port into the chamber that facilitates flushing of the chamber.

Concept 5. The needle-free connector of Concept 2 or any other Concept, wherein the compressible sealing member forms a compressible sealing member of a positive displacement valve or a negative displacement valve.

Concept 6. The needle-free connector of Concept 5 or any other Concept, further comprising at least one extension on the housing configured to prevent the compressible sealing member from obstructing the second input port in the compressed state.

Concept 7. The needle-free connector of Concept 2 or any other Concept, wherein, in the uncompressed state, the compressible sealing member forms a planar swabable surface in a common plane with a top surface of the housing.

Concept 8. The needle-free connector of Concept 1 or any other Concept, where the second input port comprises an open Luer access port.

Concept 9. The needle-free connector of Concept 8 or any other Concept, wherein the open Luer access port comprises a threaded Luer port.

Concept 10. The needle-free connector of Concept 1 or any other Concept, wherein the housing comprises a central elongate portion having a longitudinal axis, wherein the first input port comprises a needle-free valve formed along the longitudinal axis, and wherein the second input port comprises a tubular extension from a sidewall of the central elongate portion.

Concept 11. A housing for a needle-free connector, the housing comprising:
 a central elongate portion having a longitudinal axis;
 a needle-free valve formed along the longitudinal axis;
 an output port formed along the longitudinal axis;
 an open Luer port comprising an extension from a sidewall of the central elongate portion; and a chamber within the central elongate portion, wherein the chamber is fluidly coupled to the needle-free valve; the open Luer port, and the output port.

Concept 12. The housing of Concept 11 or any other Concept, further comprising first threaded features on the needle-free valve and second threaded features on the open Luer port.

Concept 13. The housing of Concept 11 or any other Concept, further comprising at least one antimicrobial eluting feature.

Concept 14. The housing of Concept 13 or any other Concept, wherein the at least one antimicrobial eluting feature comprises an antimicrobial eluting coating on an interior surface of the extension from the sidewall.

Concept 15. A patient fluid delivery system comprising:
tubing configured to provide the fluid to a patient; and
a needle-free connector configured to couple between the at least one fluid source and the tubing, the needle-free connector comprising:
a housing;
a first input port in the housing;
a second input port in the housing;
a chamber within the housing that is fluidly coupled to the first input port and the second input port;
an output port that is fluidly coupled to the chamber; and
a compressible sealing member within the housing, the compressible sealing member having an uncompressed state in which the compressible sealing member seals the first input port and a compressed state that allows a continuous fluid pathway between the first input port and the output port.

Concept 16. The patient fluid delivery system of Concept 15 or any other Concept, further comprising a catheter assembly integrally attached to the tubing.

Concept 17. The patient fluid delivery system of Concept 16 or any other Concept, wherein the catheter assembly comprises a needle hub having a paddle grip; a straight grip, or a ported grip.

Concept 18. The patient fluid delivery system of Concept 17 or any other Concept; further comprising an end cap configured to seal the second input port.

Concept 19. The patient fluid delivery system of Concept 15 or any other Concept, further comprising:
an antimicrobial coati g or an antimicrobial insert ring in the second input port; and
an antimicrobial lubricant on the compressible sealing member.

Concept 20. A method, comprising
providing a first fluid from a first input port of a needle-free connect r through a chamber of the connector to an output port of the connector; and
providing a second fluid from a second input port of the connector through the chamber to the output port.

Concept 21. The method of Concept 20 or any other Concept, wherein providing the first fluid comprises attaching a first fluid source having the first fluid to a needle-free valve formed by the first input port.

Concept 22. The method of Concept 21 or any other Concept, wherein providing the second fluid comprises attaching a second fluid source having the second fluid to an open Luer port formed by the second input port while the first fluid source is coupled to the first fluid source.

Concept 23. The method of Concept 22 or any other Concept, wherein the first fluid source and the second fluid source each comprise a needless syringe.

Concept 24. The method of Concept 23 or any other Concept, further comprising providing the first and second fluids to a patient from the output port.

Concept 25. A needle-free connector, comprising:
a lower housing having a sidewall;
a needle-free valve comprising:
an upper housing, and
a compressible sealing member disposed between the upper housing and the lower housing;
a y-port formed from a portion of the lower housing that extends at a non-parallel angle from the sidewall of the lower housing; and
an output port in the lower housing, the output port fluidly coupled to the needle-free valve and the y-port.

Concept 26. The needle-free connector of Concept 25 or any other Concept, wherein the compressible sealing member comprises a circumferential flange, and wherein the lower housing comprises an engagement feature that secures the circumferential flange between the engagement feature and an inner surface of the upper housing.

Concept 27. The needle-free connector of Concept 25 or any other Concept, further comprising an intermediate housing interposed between the upper housing and the lower housing.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender e.g., her and its and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples, A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples, A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary. Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needle-free connector, comprising:
    a housing including an upper housing and a lower housing positioned distally to the upper housing;
    a first input port in the upper housing;
    a sealing member within the housing and configured to seal the first input port;
    a second input port formed from a portion of the upper housing, and that extends along a non-parallel angle from a sidewall of the upper housing;
    at least one extension formed in the upper housing at the second input port and comprising a protrusion configured to prevent obstruction of the second input port by a portion of the sealing member extending across from the second input port;
    a chamber within the housing that is fluidly coupled to the first input port and the second input port; and
    an output port that is fluidly coupled to the chamber.

2. The needle-free connector of claim 1, wherein the sealing member comprises a compressible sealing member, the compressible sealing member having an uncompressed state in which the compressible sealing member seals the first input port and a compressed state that allows a continuous fluid pathway between the first input port and the output port.

3. The needle-free connector of claim 2, wherein the continuous fluid pathway comprises a first continuous fluid pathway and wherein the needle-free connector further comprises a second continuous fluid pathway between the second input port and the output port.

4. The needle-free connector of claim 3, further comprising a third continuous fluid pathway from the second input port into the chamber that facilitates flushing of the chamber.

5. The needle-free connector of claim 2, wherein the compressible sealing member forms a compressible sealing member of a positive displacement valve or a negative displacement valve.

6. The needle-free connector of claim 5, wherein the at least one extension is configured to prevent the compressible sealing member from obstructing the second input port in the compressed state.

7. The needle-free connector of claim 2, wherein, in the uncompressed state, the compressible sealing member forms a planar swabable surface in a common plane with a top surface of the housing.

8. The needle-free connector of claim 1, wherein the second input port comprises an open Luer access port.

9. The needle-free connector of claim 8, wherein the open Luer access port comprises a threaded Luer port.

10. The needle-free connector of claim 1, wherein the housing comprises a central elongate portion having a longitudinal axis, wherein the first input port comprises a needle-free valve formed along the longitudinal axis, and wherein the second input port comprises a tubular extension from a sidewall of the central elongate portion.

11. A housing for a needle-free connector, the housing comprising:
    an elongate portion having a longitudinal axis and defining an upper housing of the housing;

a needle-free valve formed along the longitudinal axis, the needle-free valve comprising an input port and a sealing member configured to seal the input port;
a lower housing positioned distally to the upper housing;
an output port formed along the longitudinal axis in the lower housing;
an open Luer port formed by a portion of a sidewall of the elongate portion in the upper housing;
at least one extension formed in the upper housing at the open Luer port and comprising a protrusion configured to prevent obstruction of the open Luer port by a portion of the sealing member extending across from the open Luer port; and
a chamber within the central elongate portion, wherein the chamber is fluidly coupled to the needle-free valve, the open Luer port, and the output port.

12. The housing of claim 11, further comprising first threaded features on the needle-free valve and second threaded features on the open Luer port.

13. The housing of claim 11, further comprising at least one antimicrobial eluting feature.

14. The housing of claim 13, wherein the at least one antimicrobial eluting feature comprises an antimicrobial eluting coating on an interior surface of the extension from the sidewall.

15. A patient fluid delivery system comprising:
tubing configured to provide a fluid from a fluid source to a patient; and
a needle-free connector configured to couple between the fluid source and the tubing, the needle-free connector comprising:
a housing;
a first input port in the housing;
a second input port in the housing;
a chamber within the housing that is fluidly coupled to the first input port and the second input port;
an output port that is fluidly coupled to the chamber;
a compressible sealing member within the housing, the compressible sealing member having an uncompressed state in which the compressible sealing member seals the first input port and a compressed state that allows a continuous fluid pathway between the first input port and the output port; and
at least one extension formed in the housing at the second input port and comprising a protrusion configured to prevent obstruction of the second input port by the compressible sealing member extending across from the second input port.

16. The patient fluid delivery system of claim 15, further comprising a catheter assembly integrally attached to the tubing.

17. The patient fluid delivery system of claim 16, wherein the catheter assembly comprises a needle hub having a paddle grip, a straight grip, or a ported grip.

18. The patient fluid delivery system of claim 17, further comprising an end cap configured to seal the second input port.

19. The patient fluid delivery system of claim 15, further comprising:
an antimicrobial coating or an antimicrobial insert ring in the second input port;
and an antimicrobial lubricant on the compressible sealing member.

20. A method, comprising
providing a first fluid from a first input port of a needle-free connector through a chamber of the connector to an output port of the connector; and
providing a second fluid from a second input port of the connector through the chamber to the output port,
wherein the needle-free connector comprises a housing, a sealing member, and at least one extension formed in the housing at the second input port and comprising a protrusion, and wherein the sealing member is configured to seal the first input port, and the protrusion is configured to prevent obstruction of the second input port by a portion of the sealing member extending across from the second input port.

21. The method of claim 20, wherein providing the first fluid comprises attaching a first fluid source having the first fluid to a needle-free valve formed by the first input port.

22. The method of claim 21, wherein providing the second fluid comprises attaching a second fluid source having the second fluid to an open Luer port formed by the second input port while the first fluid source is coupled to the first input port.

23. The method of claim 22, wherein the first fluid source and the second fluid source each comprise a needleless syringe.

24. The method of claim 23, further comprising providing the first and second fluids to a patient from the output port.

25. A needle-free connector, comprising:
a lower housing having a sidewall;
a needle-free valve comprising:
an upper housing, and
a compressible sealing member disposed between the upper housing and the lower housing;
a y-port, formed from a portion of the lower housing, that extends along a non-parallel angle from the sidewall of the lower housing;
at least one extension formed at the y-port and comprising a protrusion configured to prevent obstruction of the y-port by the compressible sealing member extending across the y-port; and
an output port in the lower housing; the output port fluidly coupled to the needle-free valve and the y-port.

26. The needle-free connector of claim 25, wherein the compressible sealing member comprises a circumferential flange, and wherein the lower housing comprises an engagement feature that secures the circumferential flange between the engagement feature and an inner surface of the upper housing.

27. The needle-free connector of claim 25, further comprising an intermediate housing interposed between the upper housing and the lower housing.

* * * * *